(12) United States Patent
Casey (10) Patent No.: US 8,246,674 B2
(45) Date of Patent: Aug. 21, 2012

(54) ENDOPROSTHESIS HAVING STRUTS LINKED BY FOOT EXTENSIONS

(75) Inventor: Brendan Casey, Galway (IE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

(21) Appl. No.: 12/966,916

(22) Filed: Dec. 13, 2010

(65) Prior Publication Data

US 2011/0144738 A1   Jun. 16, 2011

Related U.S. Application Data

(62) Division of application No. 11/961,754, filed on Dec. 20, 2007, now Pat. No. 7,850,726.

(51) Int. Cl.
*A61F 2/82* (2006.01)

(52) U.S. Cl. ...... 623/1.15; 623/1.1; 623/1.16; 623/1.17; 623/1.2

(58) Field of Classification Search ............ 623/1.1, 623/1.15–1.17, 1.2
See application file for complete search history.

(56) References Cited

U.S. PATENT DOCUMENTS

| | | |
|---|---|---|
| 4,475,972 A | 10/1984 | Wong |
| 4,580,568 A | 4/1986 | Gianturco |
| 4,738,740 A | 4/1988 | Pinchuk et al. |
| 4,743,252 A | 5/1988 | Martin, Jr. et al. |
| 4,759,757 A | 7/1988 | Pinchuk |
| 4,776,337 A | 10/1988 | Palmaz |
| 4,800,882 A | 1/1989 | Gianturco |
| 4,907,336 A | 3/1990 | Gianturco |
| 5,015,253 A | 5/1991 | MacGregor |
| 5,019,090 A | 5/1991 | Pinchuk |
| 5,041,126 A | 8/1991 | Gianturco |
| 5,059,211 A | 10/1991 | Stack et al. |
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |
| 5,133,732 A | 7/1992 | Wiktor |
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |

(Continued)

FOREIGN PATENT DOCUMENTS

CA   2309079   11/2004

(Continued)

OTHER PUBLICATIONS

U.S. Appl. No. 60/637,495, filed Dec. 20, 2004, Fierens et al.
U.S. Appl. No. 12/959,481, filed Nov. 18, 2010, Schneider.
U.S. Appl. No. 09/582,318, Aug. 14, 2002, Office Action.
U.S. Appl. No. 09/582,318, Mar. 7, 2003, Notice of Allowance.
U.S. Appl. No. 09/742,144, Sep. 24, 2002, Office Action.

(Continued)

*Primary Examiner* — Thomas J Sweet
*Assistant Examiner* — Yashita Sharma
(74) *Attorney, Agent, or Firm* — Workman Nydegger (57) ABSTRACT

The present invention relates to an endoprosthesis having a plurality of web rings coupled by connectors, which include two or more essentially parallel struts and a foot extension protruding from one of the struts. An endoprosthesis constructed according to the principles of the present invention provides an elevated degree of scaffolding to a body lumen while retaining an acceptable degree of flexibility.

19 Claims, 3 Drawing Sheets

U.S. PATENT DOCUMENTS

| | | | |
|---|---|---|---|
| 5,370,683 A | 12/1994 | Fontaine | |
| 5,378,239 A | 1/1995 | Termin et al. | |
| 5,380,299 A | 1/1995 | Fearnot et al. | |
| 5,421,955 A | 6/1995 | Lau et al. | |
| 5,443,458 A | 8/1995 | Eury | |
| 5,443,496 A | 8/1995 | Schwartz et al. | |
| 5,449,373 A | 9/1995 | Pinchasik et al. | |
| 5,449,382 A | 9/1995 | Dayton | |
| 5,476,508 A | 12/1995 | Amstrup | |
| 5,496,277 A | 3/1996 | Termin et al. | |
| 5,514,154 A | 5/1996 | Lau et al. | |
| 5,527,354 A | 6/1996 | Fontaine et al. | |
| 5,556,414 A | 9/1996 | Turi | |
| 5,569,295 A | 10/1996 | Lam | |
| 5,591,197 A | 1/1997 | Orth et al. | |
| 5,591,224 A | 1/1997 | Schwartz et al. | |
| 5,593,417 A | 1/1997 | Rhodes | |
| 5,593,442 A | 1/1997 | Klein | |
| 5,603,721 A | 2/1997 | Lau et al. | |
| 5,609,606 A | 3/1997 | O'Boyle | |
| 5,628,788 A | 5/1997 | Pinchuk | |
| 5,630,829 A | 5/1997 | Lauterjung | |
| 5,632,772 A | 5/1997 | Alcime et al. | |
| 5,639,278 A | 6/1997 | Dereume et al. | |
| 5,649,952 A | 7/1997 | Lam | |
| 5,651,174 A | 7/1997 | Schwartz et al. | |
| 5,653,747 A | 8/1997 | Dereume | |
| 5,670,161 A | 9/1997 | Healy et al. | |
| 5,674,242 A | 10/1997 | Phan et al. | |
| 5,674,277 A | 10/1997 | Freitag | |
| 5,693,085 A | 12/1997 | Buirge et al. | |
| 5,695,516 A | 12/1997 | Fischell et al. | |
| 5,697,971 A | 12/1997 | Fischell et al. | |
| 5,700,285 A | 12/1997 | Myers et al. | |
| 5,707,386 A | 1/1998 | Schnepp-Pesch et al. | |
| 5,707,388 A | 1/1998 | Lauterjung | |
| 5,709,703 A | 1/1998 | Lukic et al. | |
| 5,709,713 A | 1/1998 | Evans et al. | |
| 5,716,393 A | 2/1998 | Lindenberg et al. | |
| 5,723,003 A | 3/1998 | Winston et al. | |
| 5,723,004 A | 3/1998 | Dereume et al. | |
| 5,728,158 A | 3/1998 | Lau et al. | |
| 5,733,303 A | 3/1998 | Israel et al. | |
| 5,735,892 A | 4/1998 | Myers et al. | |
| 5,735,893 A | 4/1998 | Lau et al. | |
| 5,735,897 A | 4/1998 | Buirge | |
| 5,738,817 A | 4/1998 | Danforth et al. | |
| 5,741,325 A | 4/1998 | Chaikof et al. | |
| 5,741,327 A | 4/1998 | Frantzen | |
| 5,743,874 A | 4/1998 | Fischell et al. | |
| 5,749,880 A | 5/1998 | Banas et al. | |
| 5,755,771 A | 5/1998 | Penn et al. | |
| 5,755,772 A | 5/1998 | Evans et al. | |
| 5,755,774 A | 5/1998 | Pinchuk | |
| 5,755,781 A | 5/1998 | Jayaraman | |
| 5,769,884 A | 6/1998 | Solovay | |
| 5,776,161 A | 7/1998 | Globerman | |
| 5,776,181 A | 7/1998 | Lee et al. | |
| 5,776,183 A | 7/1998 | Kanesaka et al. | |
| 5,782,904 A | 7/1998 | White et al. | |
| 5,800,526 A | 9/1998 | Anderson et al. | |
| 5,807,404 A | 9/1998 | Richter | |
| 5,810,868 A | 9/1998 | Lashinski et al. | |
| 5,810,870 A | 9/1998 | Myers et al. | |
| 5,810,872 A | 9/1998 | Kanesaka et al. | |
| 5,814,063 A | 9/1998 | Freitag | |
| 5,817,126 A | 10/1998 | Imran | |
| 5,824,037 A | 10/1998 | Fogarty et al. | |
| 5,824,045 A | 10/1998 | Alt | |
| 5,824,048 A | 10/1998 | Tuch | |
| 5,824,054 A | 10/1998 | Khosravi et al. | |
| 5,824,059 A | 10/1998 | Wijay | |
| 5,827,321 A | 10/1998 | Roubin et al. | |
| 5,836,964 A | 11/1998 | Richter et al. | |
| 5,836,966 A | 11/1998 | St. Germain | |
| 5,843,120 A | 12/1998 | Israel et al. | |
| 5,843,158 A | 12/1998 | Lenker et al. | |
| 5,843,161 A | 12/1998 | Solovay | |
| 5,843,164 A | 12/1998 | Frantzen et al. | |
| 5,846,247 A | 12/1998 | Unsworth et al. | |
| 5,853,419 A | 12/1998 | Imran | |
| 5,855,598 A | 1/1999 | Pinchuk | |
| 5,855,600 A | 1/1999 | Alt | |
| 5,860,999 A | 1/1999 | Schnepp-Pesch et al. | |
| 5,861,027 A | 1/1999 | Trapp | |
| 5,868,781 A | 2/1999 | Killion | |
| 5,871,538 A | 2/1999 | Dereume | |
| 5,876,449 A | 3/1999 | Starck et al. | |
| 5,876,450 A | 3/1999 | Johlin, Jr. | |
| 5,895,406 A | 4/1999 | Gray et al. | |
| 5,897,589 A | 4/1999 | Cottenceau et al. | |
| 5,922,021 A | 7/1999 | Jang | |
| 5,928,248 A | 7/1999 | Acker | |
| 5,938,682 A | 8/1999 | Hojeibane et al. | |
| 5,948,018 A | 9/1999 | Dereume et al. | |
| 5,954,743 A | 9/1999 | Jang | |
| 5,968,091 A | 10/1999 | Pinchuk et al. | |
| 5,968,561 A | 10/1999 | Batchelder et al. | |
| 5,980,552 A | 11/1999 | Pinchasik et al. | |
| 5,984,965 A | 11/1999 | Knapp et al. | |
| 6,017,365 A | 1/2000 | Von Oepen | |
| 6,019,789 A | 2/2000 | Dinh et al. | |
| 6,027,526 A | 2/2000 | Limon et al. | |
| 6,033,433 A | 3/2000 | Ehr et al. | |
| 6,033,434 A | 3/2000 | Borghi | |
| 6,033,435 A | 3/2000 | Penn et al. | |
| 6,039,756 A | 3/2000 | Jang | |
| 6,048,361 A | 4/2000 | Von Oepen | |
| 6,059,811 A | 5/2000 | Pinchasik et al. | |
| 6,068,656 A | 5/2000 | Von Oepen | |
| 6,071,308 A | 6/2000 | Ballou et al. | |
| 6,086,610 A | 7/2000 | Duerig et al. | |
| 6,099,561 A | 8/2000 | Alt | |
| 6,106,548 A | 8/2000 | Roubin et al. | |
| 6,113,627 A | 9/2000 | Jang | |
| 6,117,165 A | 9/2000 | Becker | |
| 6,117,535 A | 9/2000 | Szycher et al. | |
| 6,123,721 A | 9/2000 | Jang | |
| 6,132,460 A | 10/2000 | Thompson | |
| 6,165,212 A | 12/2000 | Dereume et al. | |
| 6,174,326 B1 | 1/2001 | Kitakoa et al. | |
| 6,179,868 B1 | 1/2001 | Burpee et al. | |
| 6,190,403 B1 | 2/2001 | Fischell et al. | |
| 6,193,744 B1 | 2/2001 | Ehr et al. | |
| 6,193,747 B1 | 2/2001 | Von Oepen | |
| 6,200,334 B1 | 3/2001 | Jang | |
| 6,200,335 B1 | 3/2001 | Igaki | |
| 6,203,569 B1 | 3/2001 | Wijay | |
| 6,231,598 B1 | 5/2001 | Berry et al. | |
| 6,231,600 B1 | 5/2001 | Zhong | |
| 6,241,762 B1 | 6/2001 | Shanley | |
| 6,253,443 B1 | 7/2001 | Johnson | |
| 6,258,116 B1 | 7/2001 | Hojeibane | |
| 6,261,318 B1 | 7/2001 | Lee et al. | |
| 6,264,688 B1 | 7/2001 | Herklotz et al. | |
| 6,264,690 B1 | 7/2001 | Von Oepen | |
| 6,270,524 B1 | 8/2001 | Kim | |
| 6,273,913 B1 | 8/2001 | Wright et al. | |
| 6,299,604 B1 | 10/2001 | Ragheb et al. | |
| 6,299,635 B1 | 10/2001 | Frantzen | |
| 6,325,825 B1 | 12/2001 | Kula et al. | |
| 6,331,189 B1 | 12/2001 | Wolinsky et al. | |
| 6,332,089 B1 | 12/2001 | Acker et al. | |
| 6,340,366 B2 | 1/2002 | Wijay | |
| 6,348,065 B1 | 2/2002 | Brown et al. | |
| 6,377,835 B1 | 4/2002 | Schoenberg et al. | |
| 6,395,020 B1 | 5/2002 | Ley et al. | |
| 6,436,132 B1 | 8/2002 | Patel et al. | |
| 6,451,049 B2 | 9/2002 | Vallana et al. | |
| 6,485,508 B1 | 11/2002 | McGuinness | |
| 6,488,702 B1 | 12/2002 | Besselink | |
| 6,491,718 B1 | 12/2002 | Ahmad | |
| 6,503,272 B2 | 1/2003 | Duerig et al. | |
| 6,506,211 B1 | 1/2003 | Skubitz et al. | |
| 6,508,834 B1 | 1/2003 | Pinchasik et al. | |
| 6,540,776 B2 | 4/2003 | Sanders Millare et al. | |
| 6,558,415 B2 | 5/2003 | Thompson | |

| | | |
|---|---|---|
| 6,572,646 B1 | 6/2003 | Boylan et al. |
| 6,589,276 B2 | 7/2003 | Pinchasik et al. |
| 6,602,285 B1 | 8/2003 | Von Oepen et al. |
| 6,607,554 B2 | 8/2003 | Dang et al. |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,652,574 B1 | 11/2003 | Jayaraman |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,761,733 B2 | 7/2004 | Chobotov et al. |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,913,619 B2 | 7/2005 | Brown et al. |
| 6,916,336 B2 | 7/2005 | Patel et al. |
| 6,929,660 B1 | 8/2005 | Ainsworth et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2 | 10/2006 | Lowe et al. |
| 7,141,062 B1 | 11/2006 | Pinchasik et al. |
| 7,329,277 B2 | 2/2008 | Addonizio et al. |
| 7,520,892 B1 | 4/2009 | Ainsworth et al. |
| 7,625,398 B2 | 12/2009 | Clifford et al. |
| 7,686,843 B2 | 3/2010 | Moore |
| 7,789,904 B2 | 9/2010 | Von Oepen et al. |
| 7,789,905 B2 | 9/2010 | Oepen et al. |
| 7,794,491 B2 | 9/2010 | Oepen et al. |
| 7,811,314 B2 | 10/2010 | Fierens et al. |
| 7,815,672 B2 | 10/2010 | Von Oepen et al. |
| 7,815,763 B2 | 10/2010 | Fierens et al. |
| 7,842,078 B2 | 11/2010 | Von Oepen et al. |
| 7,842,079 B2 | 11/2010 | Von Oepen et al. |
| 7,846,196 B2 | 12/2010 | Von Oepen et al. |
| 7,850,726 B2 | 12/2010 | Casey |
| 7,887,577 B2 | 2/2011 | Von Oepen et al. |
| 7,887,578 B2 | 2/2011 | Schneider |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0065549 A1 | 5/2002 | White et al. |
| 2002/0107560 A1 | 8/2002 | Richter |
| 2002/0111669 A1 | 8/2002 | Pazienza et al. |
| 2002/0151964 A1 | 10/2002 | Smith et al. |
| 2002/0169499 A1 | 11/2002 | Zilla et al. |
| 2003/0055487 A1 | 3/2003 | Calisse |
| 2003/0083736 A1 | 5/2003 | Brown et al. |
| 2003/0114918 A1 | 6/2003 | Garrison et al. |
| 2003/0120334 A1 | 6/2003 | Gerbeding |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2005/0075716 A1 | 4/2005 | Yan |
| 2005/0222671 A1 | 10/2005 | Schaeffer et al. |
| 2006/0015173 A1* | 1/2006 | Clifford et al. ............... 623/1.16 |
| 2006/0106452 A1 | 5/2006 | Niermann |
| 2006/0142844 A1 | 6/2006 | Lowe et al. |
| 2006/0184232 A1 | 8/2006 | Gianotti et al. |
| 2006/0206195 A1 | 9/2006 | Calisse |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0179593 A1 | 8/2007 | Fierens et al. |
| 2007/0213800 A1 | 9/2007 | Fierens et al. |
| 2007/0299505 A1 | 12/2007 | Gregorich et al. |
| 2008/0077231 A1 | 3/2008 | Heringes et al. |
| 2008/0294239 A1 | 11/2008 | Casey |
| 2008/0294240 A1 | 11/2008 | Casey |
| 2009/0163992 A1 | 6/2009 | Osman et al. |
| 2009/0163996 A1 | 6/2009 | Bregulla |
| 2009/0163998 A1 | 6/2009 | Casey |
| 2010/0114297 A1 | 5/2010 | Calisse |
| 2011/0004289 A1 | 1/2011 | Van Oepen et al. |
| 2011/0022159 A1 | 1/2011 | Fierens et al. |

FOREIGN PATENT DOCUMENTS

| | | |
|---|---|---|
| EP | 0357003 | 3/1990 |
| EP | 0221570 | 1/1991 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7 24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/21404 | 7/1996 |
| WO | WO96/25124 | 8/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/39663 | 8/1999 |
| WO | WO99/49928 | 10/1999 |
| WO | WO00/13611 | 3/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/26164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 09/742,144, May 14, 2003, Office Action.
U.S. Appl. No. 09/742,144, Aug. 29, 2003, Notice of Allowance.
U.S. Appl. No. 09/916,394, Aug. 12, 2003, Office Action.
U.S. Appl. No. 09/916,394, Oct. 9, 2003, Office Action.

U.S. Appl. No. 09/916,394, Mar. 2, 2004, Office Action.
U.S. Appl. No. 09/967,789, Sep. 17, 2003, Office Action.
U.S. Appl. No. 09/967,789, Feb. 17, 2004, Notice of Allowance.
U.S. Appl. No. 10/241,523, Aug. 18, 2004, Office Action.
U.S. Appl. No. 10/241,523, Oct. 25, 2004, Office Action.
U.S. Appl. No. 10/241,523, Mar. 8, 2005, Office Action.
U.S. Appl. No. 10/241,523, Jun. 3, 2005, Office Action.
U.S. Appl. No. 10/241,523, Aug. 23, 2005, Office Action.
U.S. Appl. No. 10/241,523, Nov. 16, 2005, Office Action.
U.S. Appl. No. 10/241,523, Apr. 27, 2006, Office Action.
U.S. Appl. No. 10/743,857, Mar. 15, 2007, Office Action.
U.S. Appl. No. 10/743,857, Nov. 16, 2007, Office Action.
U.S. Appl. No. 10/743,857, May 8, 2008, Office Action.
U.S. Appl. No. 10/743,857, Jan. 6, 2009, Office Action.
U.S. Appl. No. 10/743,857, May 27, 2009, Office Action.
U.S. Appl. No. 10/743,857, Feb. 12, 2010, Notice of Allowance.
U.S. Appl. No. 10/743,857 Jun. 25, 2010, Notice of Allowance.
U.S. Appl. No. 10/743,857, Aug. 18, 2010, Issue Notification.
U.S. Appl. No. 10/859,636, Jun. 1, 2007, Office Action.
U.S. Appl. No. 10/859,636, Dec. 31, 2007, Office Action.
U.S. Appl. No. 10/859,636, Apr. 15, 2008, Office Action.
U.S. Appl. No. 10/859,636, Oct. 1, 2008, Notice of Allowance.
U.S. Appl. No. 10/859,636, Mar. 5, 2009, Office Action.
U.S. Appl. No. 10/859,636, Oct. 19, 2009, Notice of Allowance.
U.S. Appl. No. 10/859,636, Feb. 1, 2010, Notice of Allowance.
U.S. Appl. No. 10/859,636, May 19, 2010, Notice of Allowance.
U.S. Appl. No. 10/859,636, Dec. 9, 2010, Notice of Allowance.
U.S. Appl. No. 10/884,613, Mar. 30, 2005, Office Action.
U.S. Appl. No. 10/884,613, Nov. 14, 2005, Office Action.
U.S. Appl. No. 10/903,013, Mar. 15, 2007, Office Action.
U.S. Appl. No. 10/903,013, Nov. 19, 2007, Office Action.
U.S. Appl. No. 10/903,013, May 14, 2008, Office Action.
U.S. Appl. No. 10/903,013, Jan. 5, 2009, Office Action.
U.S. Appl. No. 10/903,013, May 27, 2009, Office Action.
U.S. Appl. No. 10/903,013, Feb. 12, 2010, Notice of Allowance.
U.S. Appl. No. 10/903,013, Jun. 24, 2010, Notice of Allowance.
U.S. Appl. No. 10/903,013, Aug. 18, 2010, Issue Notification.
U.S. Appl. No. 10/903,014, Mar. 15, 2007, Office Action.
U.S. Appl. No. 10/903,014, Nov. 16, 2007, Office Action.
U.S. Appl. No. 10/903,014, May 13, 2008, Office Action.
U.S. Appl. No. 10/903,014, Jan. 13, 2009, Office Action.
U.S. Appl. No. 10/903,014, Jun. 1, 2009, Office Action.
U.S. Appl. No. 10/903,014, Feb. 5, 2010, Notice of Allowance.
U.S. Appl. No. 10/903,014, May 26, 2010, Office Action.
U.S. Appl. No. 10/903,014, Jun. 24, 2010, Notice of Allowance.
U.S. Appl. No. 10/903,014, Aug. 25, 2010, Issue Notification.
U.S. Appl. No. 10/903,080, Mar. 15, 2007, Office Action.
U.S. Appl. No. 10/903,080, Nov. 19, 2007, Office Action.
U.S. Appl. No. 10/903,080, May 12, 2008, Office Action.
U.S. Appl. No. 10/903,080, Dec. 30, 2008, Office Action.
U.S. Appl. No. 10/903,080, May 27, 2009, Office Action.
U.S. Appl. No. 10/903,080, Jan. 13, 2010, Notice of Allowance.
U.S. Appl. No. 10/903,080, Sep. 16, 2010, Notice of Allowance.
U.S. Appl. No. 10/909,117, Aug. 22, 2007, Office Action.
U.S. Appl. No. 10/909,117, May 12, 2008, Office Action.
U.S. Appl. No. 10/909,117, Dec. 30, 2008, Office Action.
U.S. Appl. No. 10/909,117, May 27, 2009, Office Action.
U.S. Appl. No. 10/909,117, Jan. 13, 2010, Notice of Allowance.
U.S. Appl. No. 10/909,117, Sep. 16, 2010, Notice of Allowance.
U.S. Appl. No. 10/909,117, Nov. 17, 2010, Issue Notification.
U.S. Appl. No. 10/909,118, Mar. 29, 2007, Office Action.
U.S. Appl. No. 10/909,118, Nov. 19, 2007, Office Action.
U.S. Appl. No. 10/909,118, May 12, 2008, Office Action.
U.S. Appl. No. 10/909,118, Jan. 5, 2009, Office Action.
U.S. Appl. No. 10/909,118, Jul. 24, 2009, Office Action.
U.S. Appl. No. 10/909,118, Jan. 13, 2010, Notice of Allowance.
U.S. Appl. No. 10/909,118, Sep. 21, 2010, Notice of Allowance.
U.S. Appl. No. 10/954,948, Mar. 15, 2007, Office Action.
U.S. Appl. No. 10/954,948, Nov. 16, 2007, Office Action.
U.S. Appl. No. 10/954,948, May 15, 2008, Office Action.
U.S. Appl. No. 10/954,948, Jan. 13, 2009, Office Action.
U.S. Appl. No. 10/954,948, May 29, 2009, Office Action.
U.S. Appl. No. 10/954,948, Jan. 13, 2010, Notice of Allowance.
U.S. Appl. No. 10/954,948, Jul. 6, 2010, Notice of Allowance.
U.S. Appl. No. 10/955,425, Mar. 15, 2007, Office Action.
U.S. Appl. No. 10/955,425, Nov. 16, 2007, Office Action.
U.S. Appl. No. 10/955,425, May 13, 2008, Office Action.
U.S. Appl. No. 10/955,425, Jan. 13, 2009, Office Action.
U.S. Appl. No. 10/955,425, May 28, 2009, Office Action.
U.S. Appl. No. 10/955,425, Feb. 26, 2010, Notice of Allowance.
U.S. Appl. No. 10/955,425, Jun. 25, 2010, Notice of Allowance.
U.S. Appl. No. 10/955,425, Sep. 30, 2010, Issue Notification.
U.S. Appl. No. 11/313,110, Jan. 8, 2008, Office Action.
U.S. Appl. No. 11/313,110, Jul. 2, 2008, Office Action.
U.S. Appl. No. 11/313,110, Mar. 3, 2009, Office Action.
U.S. Appl. No. 11/313,110, Nov. 2, 2009, Notice of Allowance.
U.S. Appl. No. 11/313,110, Feb. 18, 2010, Notice of Allowance.
U.S. Appl. No. 11/313,110, Jun. 15, 2010, Notice of Allowance.
U.S. Appl. No. 11/313,110, Sep. 29, 2010, Issue Notification.
U.S. Appl. No. 11/404,450, Feb. 4, 2009, Office Action.
U.S. Appl. No. 11/404,450, Mar. 17, 2009, Office Action.
U.S. Appl. No. 11/404,450, Sep. 30, 2009, Office Action.
U.S. Appl. No. 11/404,450, Apr. 22, 2010, Office Action.
U.S. Appl. No. 11/404,450, Nov. 26, 2010, Office Action.
U.S. Appl. No. 11/435,260 Jan. 10, 2008, Office Action.
U.S. Appl. No. 11/435,260, Mar. 26, 2008, Office Action.
U.S. Appl. No. 11/435,260, Dec. 16, 2008, Office Action.
U.S. Appl. No. 11/435,260, Jun. 18, 2009, Notice of Allowance.
U.S. Appl. No. 11/435,260, Jun. 26, 2009, Notice of Allowance.
U.S. Appl. No. 11/601,475, Jul. 22, 2008, Office Action.
U.S. Appl. No. 11/601,475, Jan. 6, 2009, Office Action.
U.S. Appl. No. 11/601,475, Jun. 1, 2009, Office Action.
U.S. Appl. No. 11/601,475, Jan. 15, 2010, Notice of Allowance.
U.S. Appl. No. 11/601,475, Jul. 9, 2010, Notice of Allowance.
U.S. Appl. No. 11/731,820, Jan. 27, 2010, Office Action.
U.S. Appl. No. 11/731,820, Aug. 5, 2010, Notice of Allowance.
U.S. Appl. No. 11/731,820, Dec. 16, 2010, Notice of Allowance.
U.S. Appl. No. 11/731,882, Feb. 3, 2010, Office Action.
U.S. Appl. No. 11/731,882, Sep. 1, 2010, Office Action.
U.S. Appl. No. 11/732,244, Sep. 28, 2009, Office Action.
U.S. Appl. No. 11/732,244 May 5, 2010, Notice of Allowance.
U.S. Appl. No. 11/732,244, Jun. 21, 2010, Notice of Allowance.
U.S. Appl. No. 11/732,244, Sep. 22, 2010, Issue Notification.
U.S. Appl. No. 11/805,584, Apr. 27, 2009, Office Action.
U.S. Appl. No. 11/805,584, Oct. 29, 2009, Office Action.
U.S. Appl. No. 11/805,584, Mar. 15, 2010, Office Action.
U.S. Appl. No. 11/805,584, Oct. 4, 2010, Office Action.
U.S. Appl. No. 11/961,290, May 6, 2009, Office Action.
U.S. Appl. No. 11/961,290, Dec. 18, 2009, Office Action.
U.S. Appl. No. 11/961,384, May 26, 2009, Office Action.
U.S. Appl. No. 11/961,384, Oct. 8, 2009, Office Action.
U.S. Appl. No. 11/961,754, Jul. 22, 2009, Office Action.
U.S. Appl. No. 11/961,754, Apr. 5, 2010, Notice of Allowance.
U.S. Appl. No. 11/961,754, Jul. 28, 2010, Notice of Allowance.
U.S. Appl. No. 11/961,754, Nov. 23, 2010, Issue Notification.
U.S. Appl. No. 11/973,707, Jun. 9, 2009, Office Action.
U.S. Appl. No. 11/973,707, Mar. 19, 2010, Office Action.
U.S. Appl. No. 11/961,775, Oct. 1, 2009, Office Action.
U.S. Appl. No. 11/961,775, Mar. 31, 2010, Office Action.
U.S. Appl. No. 12/949,481, filed Nov. 18, 2010, Schneider.
U.S. Appl. No. 10/859,636, Mar. 30, 2011, Issue Notification.
U.S. Appl. No. 11/731,820, Mar. 30, 2011, Issue Notification.
U.S. Appl. No. 11/973,707, Oct. 12, 2011, Notice of Allowance.
U.S. Appl. No. 13/089,039, filed Apr. 8, 2011, Fierens et al.
U.S. Appl. No. 11/805,584, May 12, 2011, Office Action.
U.S. Appl. No. 11/404,450, Aug. 10, 2011, Office Action.
U.S. Appl. No. 11/731,882, Aug. 29, 2011, Notice of Allowance.
U.S. Appl. No. 11/404,450, Jan. 31, 2012, Office Action.
U.S. Appl. No. 12/895,032, Feb. 1, 2012, Office Action.
U.S. Appl. No. 12/949,481, Jan. 5, 2012, Office Action.
U.S. Appl. No. 12/949,481, Feb. 15, 2012, Office Action.
U.S. Appl. No. 11/961,384, Apr. 23, 2012, Office Action.
U.S. Appl. No. 12/875,971, Apr. 19, 2012, Office Action.
U.S. Appl. No. 11/731,882, Dec. 14, 2011, Issue Notification.

* cited by examiner

FIG. 6

ENDOPROSTHESIS HAVING STRUTS LINKED BY FOOT EXTENSIONS

CROSS-REFERENCE TO RELATED APPLICATIONS

The present application is a divisional of U.S. patent application Ser. No. 11/961,754 (Now U.S. Pat. No. 7,850,726), entitled "ENDOPROSTHESIS HAVING STRUTS LINKED BY FOOT EXTENSIONS," and filed 20 Dec. 2007. U.S. patent application Ser. No. 11/961,754 and U.S. Pat. No. 7,850,726 are each incorporated herein by reference in their entirety.

FIELD OF THE INVENTION

The present invention relates to an endoprosthesis having elevated scaffolding properties while retaining an acceptable degree of flexibility. More particularly, the present invention relates to an endoprosthesis having a plurality of web rings coupled by connectors that are composed of essentially parallel struts and that include a foot extension protruding from one of the struts.

BACKGROUND OF THE INVENTION

Stents, grafts and a variety of other endoprostheses are well known and used in interventional procedures, such as for treating aneurysms, lining or repairing vessel walls, filtering or controlling fluid flow, and expanding or scaffolding occluded or collapsed vessels. Such endoprostheses can be delivered and used in virtually any accessible body lumen of a human or animal and can be deployed by any of a variety of recognized means.

An endoprosthesis is typically delivered by a catheter system to a desired location or deployment site inside a body lumen of a vessel or other tubular organ. To facilitate such delivery, the endoprosthesis must be capable of having a particularly small crossing profile to reach the desired deployment site, which may be difficult to access by the treating physician through the tortuous pathway of the patient's anatomy. Therefore, it would be desirable to provide the endoprosthesis with a sufficient degree of longitudinal flexibility during delivery to allow advancement through the anatomy to the deployed site.

Once deployed, the endoprosthesis should be capable of satisfying a variety of performance characteristics. The endoprosthesis should have sufficient rigidity or outer bias to perform its intended function, such as opening a lumen or supporting a vessel wall. Similarly, the endoprosthesis should have suitable flexibility along its length when deployed so that it will not kink or straighten when deployed in a curved vessel. In certain application, the endoprosthesis should provide an elevated and consistent degree of scaffolding of the vessel wall and prevent plaque from protruding into the artery, for example during the treatment of atherosclerosis in the carotid arteries. Therefore, it would be desirable for the endoprosthesis to provide a substantially uniform or otherwise controlled scaffolding of the vessel wall.

One type of endoprosthesis is the stent, which is used for the treatment of atherosclerotic stenosis in blood vessels. After a patient undergoes a percutaneous transluminal angioplasty or similar interventional procedure, a stent may be deployed at the treatment site to maintain patency of the vessel. The stent is configured to scaffold or support the treated blood vessel and may be loaded with a beneficial agent, acting as a delivery platform to reduce restenosis or the like.

Numerous endoprosthesis designs and constructions have been developed to address one or more of the performance characteristics summarized above. For example, a variety of stent designs are disclosed in the following patents: U.S. Pat. No. 4,580,568 to Gianturco; U.S. Pat. No. 5,102,417 to Palmaz; U.S. Pat. No. 5,104,404 to Wolff; U.S. Pat. No. 5,133,732 to Wiktor; U.S. Pat. No. 5,292,331 to Boneau; U.S. Pat. No. 5,514,154 to Lau et al.; U.S. Pat. No. 5,569,295 to Lam; U.S. Pat. No. 5,707,386 to Schnepp-Pesch et al.; U.S. Pat. No. 5,733,303 to Israel et al.; U.S. Pat. No. 5,755,771 to Penn et al.; U.S. Pat. No. 5,776,161 to Globerman; U.S. Pat. No. 5,895,406 to Gray et al.; U.S. Pat. No. 6,033,434 to Borghi; U.S. Pat. No. 6,099,561 to Alt; U.S. Pat. No. 6,106,548 to Roubin et al.; U.S. Pat. No. 6,113,627 to Jang; U.S. Pat. No. 6,132,460 to Thompson; U.S. Pat. No. 6,331,189 to Wolinsky et al.; and U.S. Pat. No. 7,128,756 to Lowe et al., the entireties of which are incorporated herein by reference.

Figure 1:
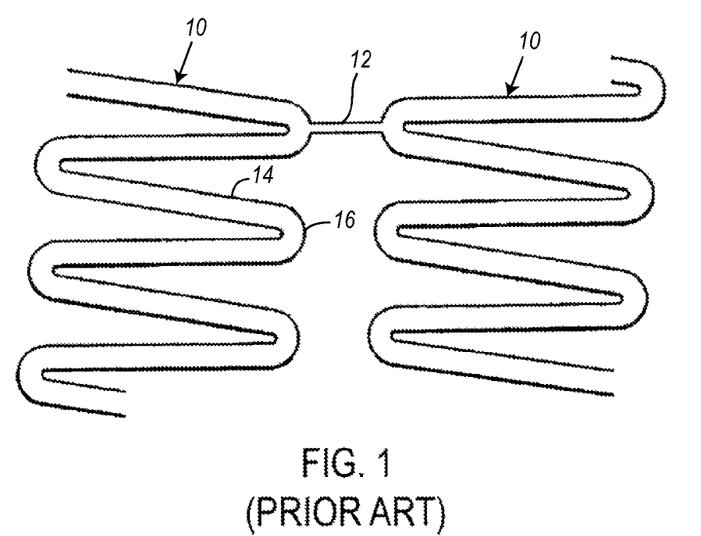
FIG. 1 illustrates a detail view of the web structure of a first endoprosthesis in the prior art.

Certain endoprosthesis structures in the prior art are based on joining a plurality of web rings disposed longitudinally with connectors that increase the flexibility of the endoprosthesis by providing preferred bending points. One example of a stent in the prior art is illustrated in FIG. 1, in which a plurality of web rings 10 (shown in a flattened configuration), are joined one to the other by connectors 12. The individual web rings 10 are formed by a plurality of web elements 14 that are sequentially adjoined at junction bends 16.

Figure 2:
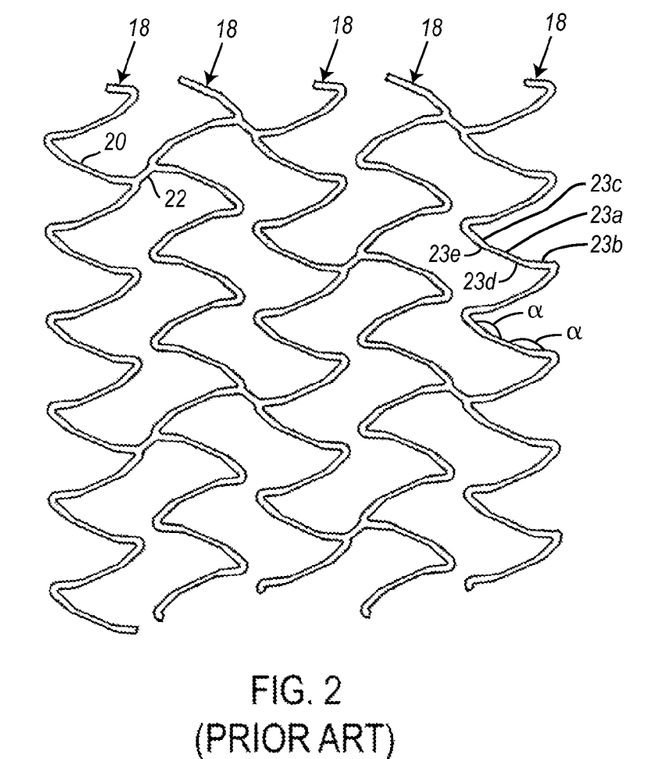
FIG. 2 illustrates a detail view of the web structure of a second endoprosthesis in the prior art.

While the endoprosthesis of FIG. 1 is shown as having web elements 14 of rectilinear design, endoprosthesis having web elements of different designs are also known in the art. For example, U.S. Patent Application Publication Nos. 2004/0193250 and 2005/0004651, U.S. Pat. Nos. 6,682,554 and 6,602,285, International Patent Publication No. WO 00/13611, and German Patent Publication No. 19840645, the entireties of which are incorporated herein by reference, disclose endoprosthesis having web elements each formed by a plurality of segments as illustrated in FIG. 2. More particularly, web rings 18 are each formed by a plurality of crown-shaped web elements 20 and are joined one to the other by connectors 22. Each of the crown-shaped web elements 20 is formed by a central member 23a, disposed essentially parallel to the longitudinal axis of the stent in the contracted delivery configuration, and by a first end member 23b and a second end member 23c extending from opposite ends (first end 23d and second end 23e) of the central member 23a at obtuse angles α.

Both of the endoprostheses of FIGS. 1 and 2 include connectors 12 and 22 that are essentially rectilinear in shape. There, those endoprostheses inherently have a limited flexibility and a limited resistance to compressive or torsional forces, for example, to the forces applied to the endoprosthesis during deployment and after implantation. In addition, connectors 12 and 22 offer limited scaffolding to the lumen walls and, if the number of connectors is increased to improve scaffolding (for example, by joining each junction bend in one web ring to a junction bend in a neighboring web ring with a connector), stent flexibility becomes proportionally decreased. Therefore, it would be desirable to provide the endoprosthesis with an elevated degree of scaffolding of the vessel wall while retaining a certain degree of flexibility.

SUMMARY OF THE INVENTION

The present invention relates to an endoprosthesis having a plurality of web rings coupled by connectors, which include two or more essentially parallel struts and a foot extension protruding from one of the struts. An endoprosthesis constructed according to the principles of the present invention provides an elevated degree of scaffolding to a body lumen while retaining an acceptable degree of flexibility.

In one embodiment, the endoprosthesis is configured as a stent defined by a web structure that is expandable from a delivery configuration to a deployed configuration and that is formed by a plurality of longitudinally adjacent web rings. Each of the web rings is defined by web elements that are disposed circumferentially around the longitudinal axis of the stent and that are sequentially adjoined at junction bends. More particularly, a first junction bend in a first web ring is connected to a second junction bend in a second web ring by a connector that includes a pair of struts essentially parallel one to the other and a foot extension joining the first to the second parallel struts.

This foot extension includes a first member that extends from the first strut and that defines the sole portion of the foot extension, and a second member that is interposed between the sole portion and the second strut and that defines the toe portion of the foot extension. Different designs of the sole and toe portions are within the scope of the present invention, for example, the sole portion may be essentially rectilinear in shape and the toe portion essentially arcuate.

In one embodiment, the foot extension couples the first and the second struts of the connector to the second junction bend.

In another embodiment, a second foot extension also couples the first and the second struts of the connector and is aligned circumferentially with, but in a direction opposite to, the first foot extension.

In still another embodiment, a second foot extensions couples the first and the second struts of the connector to the first junction bend.

In still another embodiment, another foot extension protrudes from the first junction bend and couples the first web ring to the connector.

In still another embodiment, another foot extension protrudes from the second junction bend and couple the second web ring to the connector.

Other foot extensions may protrude from junction bends of the web rings that are not coupled to the connector.

The struts of the connector may be rectilinear in shape or have multi-segment or curved profiles. The struts of the web rings may also be rectilinear in shape, or may include a central member and first and second end members extending from the central member at an obtuse angle to form a crown shape. In the latter embodiment, the web elements are nested one into the other in the contracted delivery configuration and the web elements of neighboring web rings may be oriented at approximately 180 degrees in relation to each other.

The endoprosthesis of the present invention may be configured to self-expand from the contracted delivery configuration to the expanded deployed configuration, or may be deployed by applying a radial pressure to an interior surface of the endoprosthesis, for example, by inflating a balloon disposed within the endoprosthesis.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to use the present invention in virtually any detailed system, structure or manner.

The present invention relates to an endoprosthesis for delivery within a body lumen that is formed by a plurality of web rings coupled by connectors, which include two or more essentially parallel struts and a foot extension protruding from one of the struts. Additional foot extensions may also protrude from the web rings.

An endoprosthesis constructed according to the principles of the present invention provides an elevated degree of scaffolding to a body lumen but retains an acceptable degree of flexibility. The endoprosthesis may be configured as a stent, graft, valve, occlusive device, trocar or aneurysm treatment device and may be used for a variety of intralumenal applications, including vascular, coronary, biliary, esophageal, renal, urological and gastrointestinal. For ease of description and without restrictive intent, an embodiment of the present invention will be described hereinafter with reference to a stent.

Figure 3:
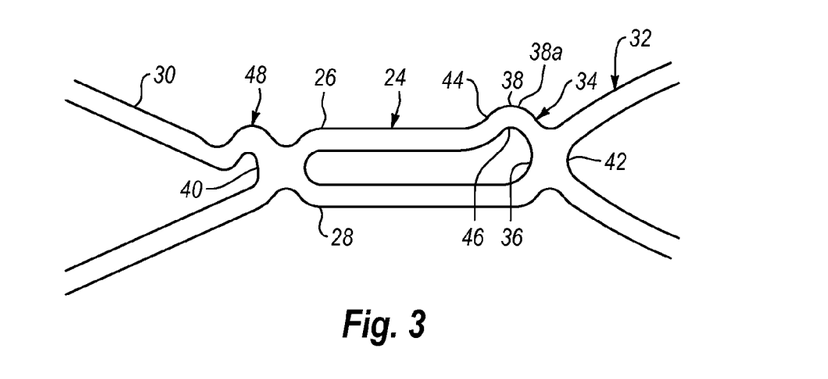
FIG. 3 illustrates a connector having struts linked by a foot extension according to a first embodiment of the invention.

FIG. 3 illustrates a connector 24 that connects a first web ring 30 to a second web ring 32 in a stent and that includes two essentially parallel struts 26 and 28. While struts 26 and 28 are shown as rectilinear in shape, struts 26 and 28 may each be formed by a plurality of segments to provide a "V", "W", or similar shape, or may be curved. FIG. 3 also shows that struts 26 and 28 may connect first and second web rings 30 and 32 at points that are longitudinally aligned, providing connectors 24 with a direction essentially parallel to the longitudinal axis of the stent after the stent is expanded. In other embodiments, connectors 24 may have a transversal direction in relation to the longitudinal axis of the stent after expansion, in the manner shown in FIG. 2.

A foot extension 34 couples strut 26 to strut 28 at one end of connector 24 and includes a sole portion 36 that continues into a toe portion 38, having an apex 38a, which is interposed between sole portion 36 and strut 26. Sole portion 36 and toe portion 38 may each have a variety of shapes, providing foot extension 34 with a variety of configurations. For example, sole portion 36 may be essentially rectilinear with curved end connections to struts 26 and 28, or have an arcuate shape, while toe portion 38 instead may be arcuate in shape, as shown in FIG. 3, or have a multi-segmented shape. Different possible configurations of the sole and toe portions of a foot extension are disclosed in U.S. Pat. No. 7,128,756 to Lowe et al. and in U.S. Patent Application Publication Nos. 2005/0107865 to Clifford et al., 2006/0015173 to Clifford et al., 2006/0142844 to Lowe et al., 2007/0021834 to Young et al., and 2007/0021827 to Lowe et al., the entireties of which are incorporated herein by reference.

As shown in FIG. 3, connector 24 couples a first junction bend 40 on first web ring 30 to a second junction bend 42 on second web ring 32. Also as shown in FIG. 3, foot extension 34 may be positioned on connector 24 to operate as the coupling area between connector 34 and junction bend 42, causing sole portion 36 and junction bend 42 to be integrally adjoined.

Connector 24 provides the stent with improved radial strength and also with improved scaffolding properties due to the two parallel struts included within connector 24 as compared to stents having connectors with a single strut; for example, as compared to the stents depicted in FIGS. 1 and 2. Further, the increased stent surface density provided by the pair of struts 26 and 28 in comparison with single strut connectors provides an additional barrier to prevent plaque from protruding into the artery.

While providing increased scaffolding properties, connector 24 retains a level of flexibility that is adequate for a variety of angioplasty applications because foot extension 34 includes areas of flexure 44 and 46. Moreover, foot extension 34 provides the stent with a lower risk of sliding after the stent is crimped on a balloon than a straight connector, because resistance to sliding increases in proportion to the amount of metal segments disposed circumferentially in relation to metal segments extending longitudinally.

Both struts 26 and 28 and foot extension 34 are produced from the same material, but in one embodiment of the invention, one of the two struts 26 or 28 is produced from a durable material while the other strut is produced from a biodegradable material. For example, strut 26 may be produced from a metal material such as stainless steel or Nitinol (when the stent is self-expanding), while strut 28 may be produced from a polylactic acid (a biodegradable polyester derived from lactic acid). Either or both of struts 26 or 28 may also be coated with a therapeutic material, for example, a restenosis-inhibiting material or an immunosuppressant such as everolimus.

Figure 3A:
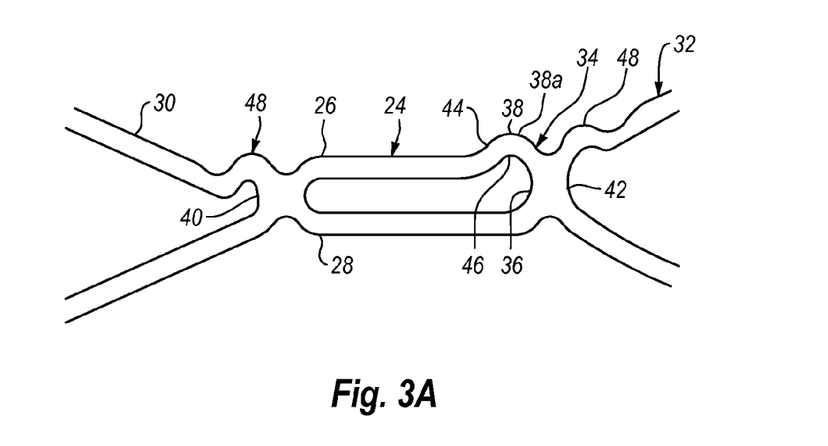
FIG. 3A illustrates a connector having struts linked by a foot extension according another embodiment of the invention.
Figure 4:
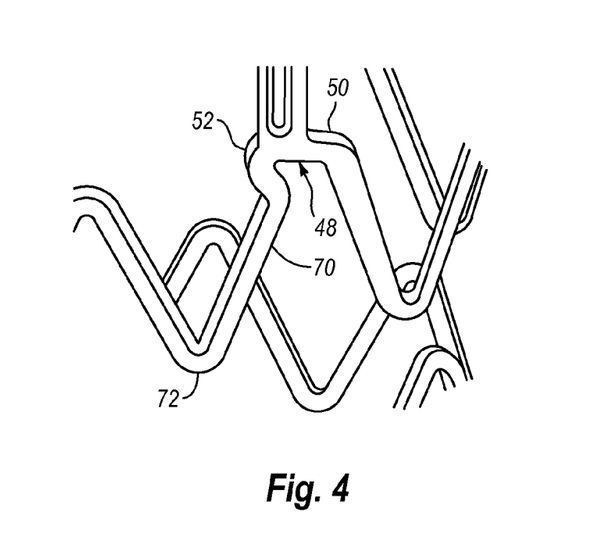
FIG. 4 illustrates a detail view of a web ring in a variant of the embodiment of FIG. 3.

Referring now to FIGS. 3 and 4, a foot extension 48 may also be positioned in first web ring 30, as shown in FIG. 3, and/or in second web ring 32, as shown in FIG. 3A. Foot extension 48 may have the same profile as foot extension 34 situated in connector 24 or may have a different profile. For example, as shown in FIG. 4, foot extension 48 may include a sole portion 50 essentially rectilinear in shape and a toe portion 52 essentially arcuate in shape, but any of the foot extension profiles previously described with regard to connector 24 may be used in first web ring 30.

It should be noted that foot extensions 48 are not necessarily disposed on first web ring 30 and/or 32 only at the junctions with connectors 24, but may be present also in parts of web rings 30 and/or 32 that are not coupled to connectors 24. Examples of possible dispositions of foot extensions 48 on web rings are disclosed in the above mentioned U.S. Pat. No. 7,128,756 to Lowe et al. and in U.S. Patent Application Publication Nos. 2005/0107865 to Clifford et al., 2006/0015173 to Clifford et al., 2006/0142844 to Lowe et al., 2007/0021834 to Young et al., and 2007/0021827 to Lowe et al.

Figure 5:
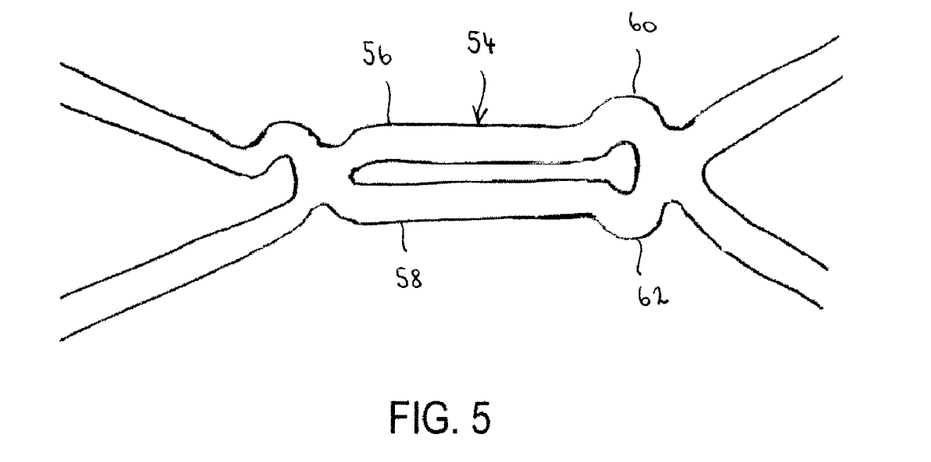
FIG. 5 illustrates a connector having struts linked by foot extensions according to a second embodiment of the invention.
Figure 6:
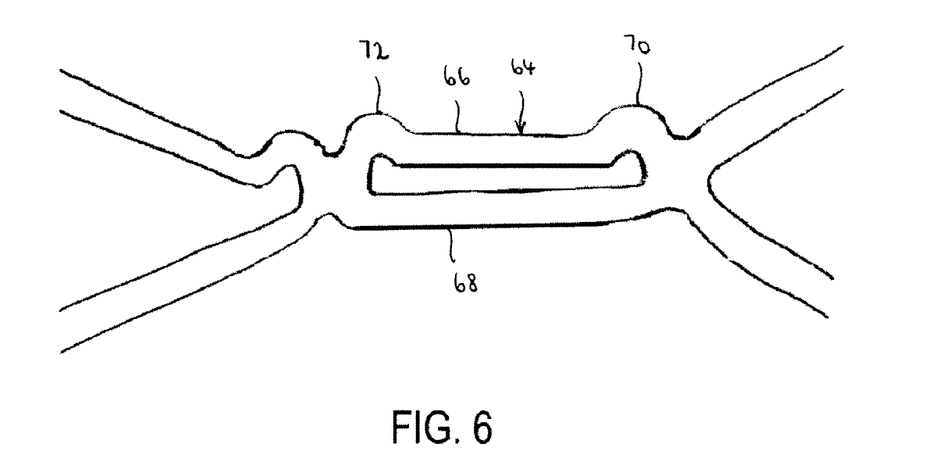
FIG. 6 illustrates a connector having struts linked by foot extensions according to a third embodiment of the invention.

Referring now to FIGS. 5 and 6, other embodiments of the invention include connectors that have a plurality of foot extensions. More particularly, FIG. 5 illustrates an embodiment of the invention, in which a connector 54 includes first strut 56 and second strut 58, disposed essentially one parallel to the other, and first foot extension 60 and second foot extension 62 disposed one opposite to the other, with foot extension 60 protruding from strut 56 and foot extension 62 protruding from strut 58. This design provides the stent with greater ability to absorb torsional stresses than the design of FIG. 3.

Another embodiment of the invention is illustrated in FIG. 6, in which connector 64 includes first strut 60 and second strut 68 disposed one parallel to the other and also includes first foot extension 70 and second foot extensions 72 both protruding from opposite ends of strut 66. This design provides the stent with greater ability to absorb bending stresses than the design of FIG. 3.

The embodiments of FIGS. 3-6 are to be considered non-limiting, and other embodiments of the invention may include foot extensions that protrude from each of the connectors struts but that are not aligned circumferentially, or more than two foot extensions disposed on different points of the connector.

In each of the embodiments of FIGS. 5 and 6, foot extensions may also be disposed on the first and/or second web rings, in the same manner as described with regard to the embodiment of FIG. 3.

The embodiments described hereinbefore have been illustrated with regard to web elements formed by essentially rectilinear struts 70, as shown in FIG. 4, which are sequentially joined either by junction bends 72 or by foot extensions 48.

It should be noted that the connector of the present invention finds equal applicability in web rings formed by web elements of different shapes. For example, the web elements may be shaped as the crowns illustrated in FIG. 2, in which each of the web elements is formed by a central member, disposed essentially parallel to the longitudinal axis of the stent in the contracted delivery configuration, and by a first and a second end members extending from opposite ends of the central member at obtuse angles. Such obtuse angles may be the same or different. The crowns are joined sequentially with junction bends that have arcuate shapes and, in the contracted delivery configuration, are nested one into the other. The crowns of neighboring web rings may be disposed in opposite directions, that is, the crowns in one web ring may be disposed at 180 degrees compared to the crowns of a neighboring web ring.

A person skilled in the art will appreciate that web elements of still different shapes may be employed in constructing the web rings and that such alternative designs all fall within the spirit and scope of the present invention.

The web rings of the endoprosthesis may be manufactured from a variety of biocompatible materials known in the art, including metal and plastic materials, and may be deployed at a target vessel using techniques also known in the art, either by inflating a balloon coupled to the catheter or, if the endoprosthesis is manufactured from a shape memory material such as Nitinol (a nickel-titanium alloy), by allowing the endoprosthesis to self-expand until contact with the vessel wall is established.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An endoprosthesis for delivery in a body lumen comprising:
   a web structure defining an essentially tubular body expandable from a contracted configuration to an expanded configuration;
   a plurality of longitudinally adjacent web rings defining the web structure; and
   a plurality of sequentially adjoined web elements defining the web rings, the web elements being disposed substantially parallel to a longitudinal axis of the essentially tubular body when in the contracted configuration, pairs of the web elements being sequentially adjoined at junction bends,
   wherein a first junction bend in a first web ring is connected to a second junction bend in a second web ring by a connector having a first strut and a second strut, the first strut and second strut being essentially parallel one to the other with a space between at least a portion of the first strut and the second strut,
   the connector having at least a first foot extension joining the first strut to the second strut at the second junction bend,
   the first foot extension including a first member extending from the first strut and providing a sole portion of the first foot extension, and a second member interposed between the sole portion and the second strut and providing the toe portion of the first foot extension, the toe portion of the first foot extension extending away from the second junction bend in a direction transverse to the longitudinal axis, with an apex of the toe portion being spaced apart from the second web ring,
   wherein the sole portion has an essentially rectilinear shape and the toe portion has an essentially arcuate shape, and
   wherein the first junction bend forms a closed cell with the first strut, the second strut, and the first foot extension.

2. The endoprosthesis of claim 1, wherein the first foot extension couples the first and the second struts of the connector to the second junction bend.

3. The endoprosthesis of claim 2, further comprising a second foot extension joining the first to the second struts, wherein the second foot extension is aligned circumferentially with and disposed in a direction opposite to the first foot extension.

4. The endoprosthesis of claim 2, further comprising a second foot extension joining the first to the second parallel struts, wherein the second foot extension couples the first and the second struts of the connector to the first junction bend.

5. The endoprosthesis of claim 1, wherein the first web ring comprises the foot extension at the first junction bend.

6. The endoprosthesis of claim 1, wherein the endoprosthesis is a stent.

7. The endoprosthesis of claim 1, wherein the first and the second struts are rectilinear.

8. The endoprosthesis of claim 1, wherein the first and the second struts have multi-segment or curved profiles.

9. The endoprosthesis of claim 1, wherein the web elements are rectilinear in shape.

10. The endoprosthesis of claim 1,
    wherein each of the web elements comprises a central member having a first and a second ends,
    wherein the central member is disposed essentially parallel to the longitudinal axis in the contracted configuration,
    wherein a first end member extends from the central member at a first obtuse angle between the first end member and the central member, and
    wherein a second end member extends from the central member at a second obtuse angle between the second end member and the central member.

11. The endoprosthesis of claim 10, wherein the first and the second obtuse angles are essentially equal.

12. The endoprosthesis of claim 10, wherein the web elements of each web ring are nested one into the other in the contracted delivery configuration, and wherein the junction bends have an arcuate shape.

13. The endoprosthesis of claim 10, wherein the web elements in the first web ring are oriented at approximately 180 degrees in relation to the web elements in the neighboring web ring.

14. The endoprosthesis of claim 1, wherein the web structure is configured to self-expand from the contracted configuration to the expanded configuration.

15. The endoprosthesis of claim 1, wherein the web structure is configured to expand from the contracted configuration to the expanded configuration by application of a radial pressure to an interior surface of the essentially tubular body.

16. An endoprosthesis for delivery in a body lumen comprising:
    a web structure defining an essentially tubular body expandable from a contracted configuration to an expanded configuration;
    a plurality of longitudinally adjacent web rings defining the web structure; and
    a plurality of sequentially adjoined web elements defining the web rings, the web elements being disposed substantially parallel to a longitudinal axis of the essentially tubular body when in the contracted configuration, pairs of the web elements being sequentially adjoined at junction bends,
    wherein a first junction bend in a first web ring is connected to a second junction bend in a second web ring by a connector having a first strut and a second strut, the first strut and second strut being essentially parallel one to the other with a space between at least a portion of the first strut and the second strut,
    the connector having at least a first foot extension joining the first strut to the second strut at the second junction bend,
    the first foot extension including a first member extending from the first strut and providing a sole portion of the first foot extension, and a second member interposed between the sole portion and the second strut and providing the toe portion of the first foot extension, the toe portion of the first foot extension extending away from the second junction bend in a direction transverse to the longitudinal axis, with an apex of the toe portion being spaced apart from the second web ring,
    wherein the sole portion has an essentially rectilinear shape and the toe portion has an essentially arcuate shape, and
    wherein a second foot extension protrudes from the first junction bend and couples the first web ring to the connector, the second foot extension forming a closed cell with the first strut, the second strut, and the first foot extension.

17. The endoprosthesis of claim 16, wherein the endoprosthesis is a stent.

18. The endoprosthesis of claim 16, wherein the first and the second struts are rectilinear.

19. An endoprosthesis for delivery in a body lumen comprising:
- a web structure defining an essentially tubular body expandable from a contracted configuration to an expanded configuration;
- a plurality of longitudinally adjacent web rings defining the web structure; and
- a plurality of sequentially adjoined web elements defining the web rings, the web elements being disposed substantially parallel to a longitudinal axis of the essentially tubular body when in the contracted configuration, pairs of the web elements being sequentially adjoined at junction bends,
- wherein a first junction bend in a first web ring is connected to a second junction bend in a second web ring by a connector having a first strut and a second strut, the first strut having a first end and a second end, the second strut having a first end and a second end, the first strut and second strut being essentially parallel one to the other with a space between at least a portion of the first strut and the second strut,
- the connector having at least a first foot extension joining the first strut to the second strut at the second junction bend,
- the first foot extension including a first member extending from the second end of the first strut and providing a sole portion of the first foot extension, and a second member extending from the second end of the second strut and being interposed between the sole portion and the second strut and providing the toe portion of the first foot extension, the toe portion of the first foot extension extending away from the second junction bend in a direction transverse to the longitudinal axis and extending away from the second end of the second strut in a direction transverse to the longitudinal axis, with an apex of the toe portion being spaced apart from the second web ring,
- wherein the sole portion has an essentially rectilinear shape and the toe portion has an essentially arcuate shape, and
- wherein a second foot extension protrudes from the first junction bend and couples the first web ring to the connector, the second foot extension forming a closed cell with the first strut, the second strut, and the first foot extension.

* * * * *